(12) United States Patent
Pan et al.

(10) Patent No.: US 10,285,972 B2
(45) Date of Patent: May 14, 2019

(54) TRANS-2-NONADECYL-4-HYDROXY-METHYL-1,3-DIOXOLANE AND PRODUCING METHOD THEREOF

(71) Applicants: Greenyn Biotechnology Co., Ltd, Taichung (TW); Min-Hsiung Pan, Kaohsiung (TW)

(72) Inventors: Min-Hsiung Pan, Kaohsiung (TW); Chi-I Chang, Pingtung County (TW); Chia-Feng Wu, Taichung (TW); Pang-Kuei Hsu, Taichung (TW)

(73) Assignees: GREENYN BIOTECHNOLOGY CO., LTD, Taichung (TW); Min-Hsiung Pan, Kaohsiung (TW)

( * ) Notice: Subject to any disclaimer, the term of this patent is extended or adjusted under 35 U.S.C. 154(b) by 0 days.

(21) Appl. No.: 15/228,202

(22) Filed: Aug. 4, 2016

(65) Prior Publication Data
US 2016/0338994 A1 Nov. 24, 2016

(30) Foreign Application Priority Data

Jan. 23, 2014 (TW) .............................. 103102539 A (51) Int. Cl.
*A61K 31/357* (2006.01)
*C07D 317/20* (2006.01)

(52) U.S. Cl.
CPC .......... *A61K 31/357* (2013.01); *C07D 317/20* (2013.01)

(58) Field of Classification Search
CPC ................................................... C07D 317/20
See application file for complete search history.

(56) References Cited

U.S. PATENT DOCUMENTS

2010/0099894 A1   4/2010   Dubois et al.

FOREIGN PATENT DOCUMENTS

TW  201114465 A  *  1/2011
TW  201114465 A1    5/2011

OTHER PUBLICATIONS

Allen et al, Ansel's pharmaceutical dosage forms and drug delivery systems, Tenth Edition, 2014.*
Carey et al, Nonalcoholic Fatty Liver Disease, Cleveland, Mar. 2013.*
Martyn et al. ("Obesity-induced Insulin Resistance and Hyperglycemia: Etiologic Factors and Molecular Mechanisms"; 2008; Anesthesiology; Warner, et al., Eds.; 109:137-48).*
Hayashi et al, Falk workshop, prevention of progression of chronic liver disease, copyright 2004.*
Chiang et al, Am J Physiol Gastrointest Liver Physiol. May 2011; 300(5): G697-G702 (Year: 2011).*
Veeresa Gududuru, et al., Identification of Darmstoff analogs as selective agonists and antagonists of lysophosphatidic acid receptors., Bioorganic & Medcinal Chemistry Letters, 2006, vol. 16, pp. 451-456.
Violeta R.Ruiz, et al., Gold catalysts and solid catalysts for biomass transformations: valorization of glycerol and glycerol-water mixtures through formation of cyclic acetals, Journal of Catalysis, 2001, vol. 271, pp. 351-357.
C. Broquet, et al., Aminoacylates and aminocarbamates of 2-substituted 4-hydroxymethyl 1,3-dioxolans as ammonium salts. A new series of PAF antagonists, Eur J Med Chem, 1990, vol. 25, pp. 235-240.

\* cited by examiner

*Primary Examiner* — Jean P Cornet
(74) *Attorney, Agent, or Firm* — Muncy, Geissler, Olds & Lowe, P.C.

(57) ABSTRACT

The present invention discloses a method for producing trans-2-nonadecyl-4-hydroxymethyl-1,3-dioxolane comprising mixing alkanes and pyridinium chlorochromat for an oxidation reaction; obtaining a product by the oxidation reaction for processing an aldolization reaction and then purifying for obtaining a trans-2-nonadecyl-4-hydroxymethyl-1,3-dioxolane compound. According to the method of the present invention, it is able to promote the productivity and reduce the cost.

5 Claims, 14 Drawing Sheets

TRANS-2-NONADECYL-4-HYDROXY-METHYL-1,3-DIOXOLANE AND PRODUCING METHOD THEREOF

FIELD OF THE INVENTION

The present invention relates to a method for producing compound and its uses, especially relates to a use of trans-2-nonadecyl-4-hydroxymethyl-1, 3-dioxolane and producing method thereof.

DESCRIPTION OF THE RELATED ART

Liver diseases have apparently become an important concern to modern people. More specifically, the factors like alcohol, medicine, drug or virus can cause the chronic inflammation of liver parenchyma continuously or repeatedly happened. It results in lasting damages, even necrosis, about liver cells and engages the individual in high risks of liver diseases like fatty liver or liver cirrhosis, even has an extremely high risk to become liver cancer. Liver fibrosis is a pathological symptom of chronic liver damage. The main cause lies on proliferation and decomposition of liver fibrillar connective tissues which were under an unbalance status and over-accumulated liver extracellular matrixes when liver cells suffered last and long damages. Liver fibrosis is also an essential process for that the chronic liver diseases turn to the liver cirrhosis or the liver cancer. Liver fibrosis is not an irreversible process, so there are few effective drugs, such as colchicine, adrenal cortex hormones and interferon, provided to treat it. However, said drugs can't performance free from side effects and can merely block partial symptoms of liver fibrosis, but not to inhibit all of it. Besides of western medicines, there are many Chinese herbs to treat liver fibrosis in traditional Chinese medicine, for examples, danshen root, radix notoginseng, turtle shell, starwort root, etc. Chinese herbs can decrease side effect to the individual, but it have to take times to perform drug effect, lead to more costs, and the effectiveness of Chinese herbs will be disturbed by jumbled ingredient from unknown sources.

Besides, some kinds of food have immune enhance function to treat liver diseases, generally like clams. However, it needs to eat large amount of clams to perform the effectiveness. So, there are clinical difficulties to treat diseases. In order to avoid said defects, Taiwan patent no. I370747 revealed a method to purify the extraction of clams from alcohol in column to extract a compound which is active to against liver fibrosis. But the method described in the prior art needs to gather the active compound through complicated processes. In other words, the method revealed in the prior art includes following problems. First, it needs large amount of clams as materials and leads to extremely high costs of production. Second, it needs at least two steps to purify the active compound, so the productivity is too low.

Therefore, it still lacks an effective compound which has specific effectiveness for liver fibrosis and less side effect in revealed prior art. So far, the most important subject is to develop a compound which is low production costs, less side effect and effective to inhibit liver fibrosis for clinical treatment of liver diseases.

SUMMARY OF THE INVENTION

The major purpose of the present invention is to provide a method for treating or/and preventing a metabolic disease selected from the group consisting of obesity, fatty liver and liver fibrosis.

In an embodiment of this present invention, the method comprises administering a subject an effective amount of a compound of formula (I):

In another embodiment of this present invention, the effective amount of the compound of formula (I) is 40 mg/day to 100 mg/day.

In one embodiment of this present invention, the effective amount of the compound of formula (I) is 90 mg/day to 100 mg/day.

Furthermore, the compound of formula (I) is obtained by acetalization reaction of the compounds of formula (II):

and formula (III):

In an embodiment of this present invention, the compound of formula (II) is produced by the oxidation reaction of the compound of the formula (IV):

and the pyridinium chlorochromate in organic solvent.

In an embodiment of this present invention, an acidic catalyst is used during the acetalization reaction.

In an embodiment of this present invention, the compound of formula (I) can be purified by separation process, wherein the isolation process includes, but not limited to, chromatography, salt out or other method which is recognized by a person of ordinary skill in the art.

In addition, the compound of formula (I) can be made to food, supplement, nutrient composition, or medicine.

DETAILED DESCRIPTION OF THE INVENTION

The present invention is further described with the following examples and figures.

Example 1: Production of the Compound TNHD of Formula (I)

Firstly, equal amount of the compound of formula (IV):

and pyridinium chlorochromate (hereafter referred to as PCC) were dissolved in dichloromethane, and then stirred and mixed it all together, wherein, at this present example, the amount of the compound of formula (IV) or PCC was 1 gram, and the amount of dichloromethane was 20 ml. The dichloromethane solution containing the compound of formula (IV) and PCC was suction filtered through Celite to obtain a filtrate, and then the filtrate was condensed under a reduced pressure to have the compound of formula (II):

which was a white solid. The aforesaid reaction is shown as the following chemical equation:

50 ml of toluene was as solvent to dissolve the compound of formula (II), and then added 700 mg of the compound of the formula (III):

and 300 mg of p-toluenesulfonic acid (TsOH). The toluene solution containing the compound of formula (II), the compound of the formula (III) and p-toluenesulfonic acid (TsOH) was heated to reflux for about 3 hours. After that, the toluene solution was removed the toluene therein by condensing under a reduced pressure, then added aqueous solution of sodium carbonate ($Na_2CO_3$) containing 1% by weight of sodium carbonate for 20 ml and then extracted 3 times by ethyl acetate. The extracts were collected and removed ethyl acetate by condensing under a reduced pressure to have a mixture containing the compound TNHD of formula (I)

The aforesaid reaction is shown as the following chemical equation:

In order to purify the compound of formula (I), the mixture was dissolved at 5 ml of hexane and then separated the white compound of formula (I) about total 260 mg by silica gel column chromatography, wherein the elution buffer used in the silica gel column chromatography was hexane/ethyl acetate (9:1).

Example 2: Purification of the Active Component for Liver Protection from Clams

With reference to the description of the related prior art, removing the clamshells from 65 kg of clams to have clam bodies were about 27.7 kg. After drying by heated-wind, the weight of the dried clam bodies was about 2.5 kg, and then extracted by soaking into alcohol which weight was three-fold as much as the weight of the clam dried bodies. Obtaining a clam-alcohol extract was about 1 kg.

900 grams of the clam-alcohol extract, water and ethyl acetate were mixed at the volume ratio 1:1:1, and then separating and extracting it by separating funnel to obtain an ethyl acetate layer. The ethyl acetate layer was condensed and frozen to obtain a clam-alcohol-ethyl-acetate extract. 900 grams of the ethyl acetate layer was separated by using chromatography column with the porous silicone gel (40~63 pores), and sequentially eluted with the solutions of hexanol and ethyl acetate at the volume ratio of 10:1, 5:1, 3:1, 1:1, 1:3, 1:5 and 1:10 and methanol, and then 18 fragments were taken. The 18 fragments were analyzed by thin layer chromatography (TLC) to isolate an active component about 1 gram, wherein, liver protection effect of the active component was disclosed in Taiwan patent no. I340747, so there will be no more description about this matter.

The active component has the following characteristics: white and solid, the melting point about 51° C., the specific rotatory power: [α]D25+1.15 (c=0.75, methanol). Rf value of the active component is 0.3 by TLC under the condition of hexanol and ethyl acetate at the volume ratio of 4:1. Moreover, analyzed by hydrogen nuclear magnetic resonance spectroscopy ($^1$H-NMR) and carbon-13 nuclear magnetic resonance spectroscopy ($^{13}$C-NMR), the spectrums of the active component are shown as FIG. 1 and FIG. 2, wherein deuterated chloroform (CDCl$_3$) was used as a solvent and the frequency was 400 MHz.

Figure 1:
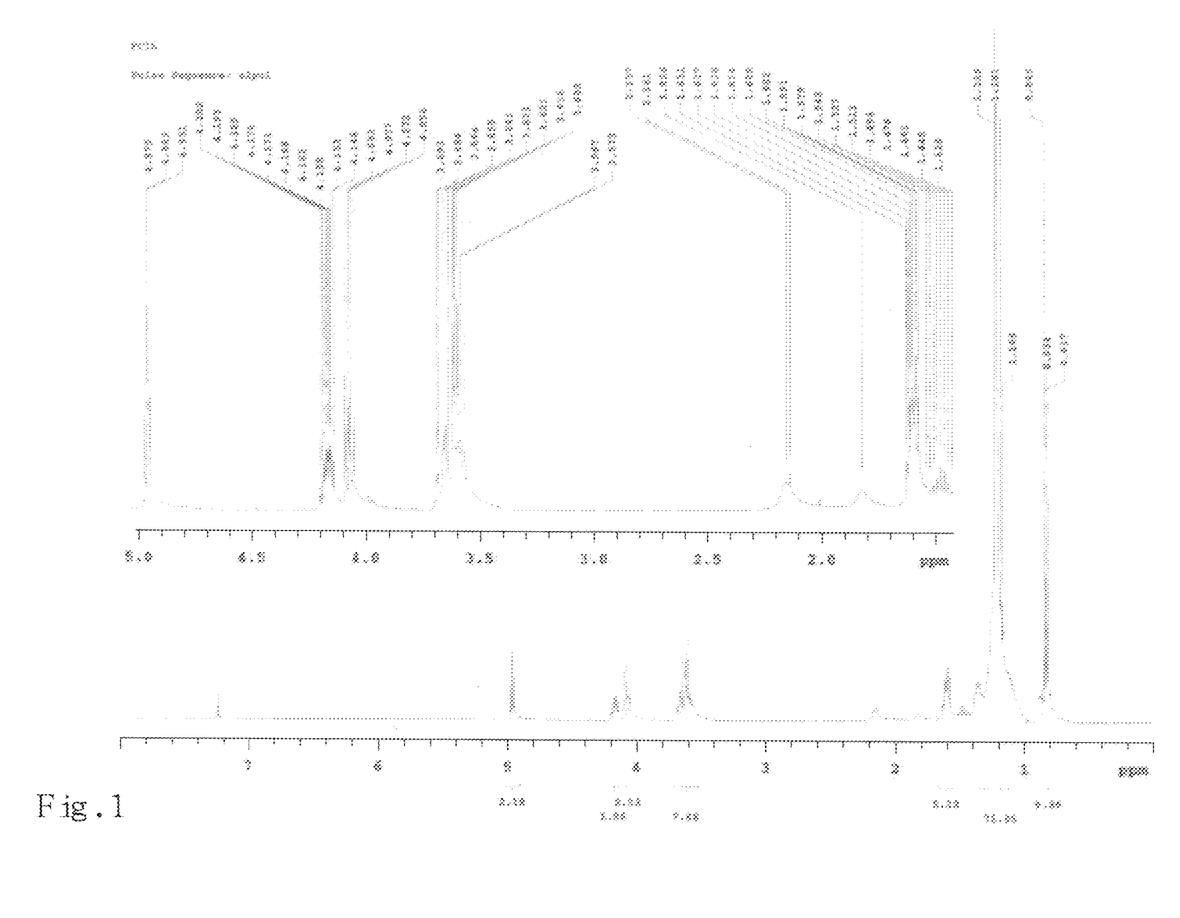
FIG. 1 is the $^1$H-NMR spectrogram of the active material from example 2 in this present invention.
Figure 2:
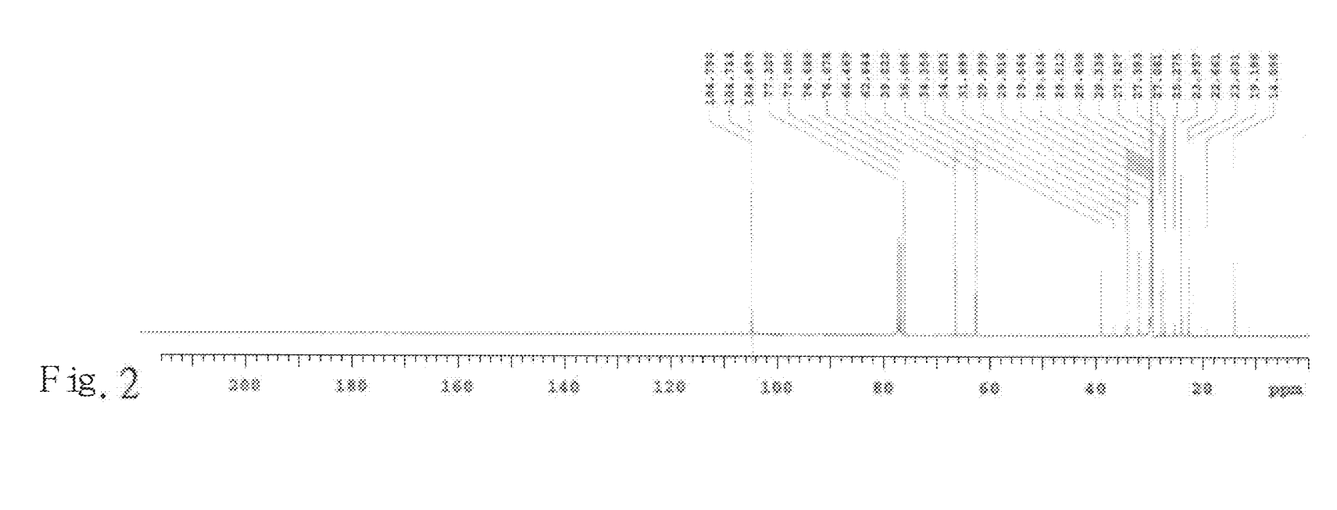
FIG. 2 is the $^{13}$C-NMR spectrogram of the active material from example 2 in this present invention.

According to FIG. 1, it shows that $\delta_H$ values of the active component were 4.96 (1H, t, J=4.8 Hz, H-2), 4.17 (1H, m, H-4), 4.08 (1H, dd, J=8.4, 6.4 Hz, H-5a), 3.67 (1H, dd, J=11.6, 3.6 Hz, H-6b), 3.62 (1H, dd, J=8.4, 7.2 Hz, H-5b), 3.58 (1H, dd, J=11.6, 5.6 Hz, H-6b), 2.15 (1H, br. s, 6-OH), 1.59-1.63 (2H, m, H-1'), 1.27-1.43 (2H, m, H-2'), 1.01-1.25 (32H, br s, H-3'-18'), 0.87 (t, 3H, J=6.6 Hz, H-19'). According to FIG. 2, it shows that $\delta_c$ values of the active component were 104.7 (C-2), 76.1 (C-5), 66.5 (C-4), 62.6 (C-6), 34.1 (C-1'), 31.9 (C-17'), 29.3-29.9 (C-3'-16'), 24.0 (C-2'), 22.7 (C-18'), 14.1 (C-19').

Figure 3:
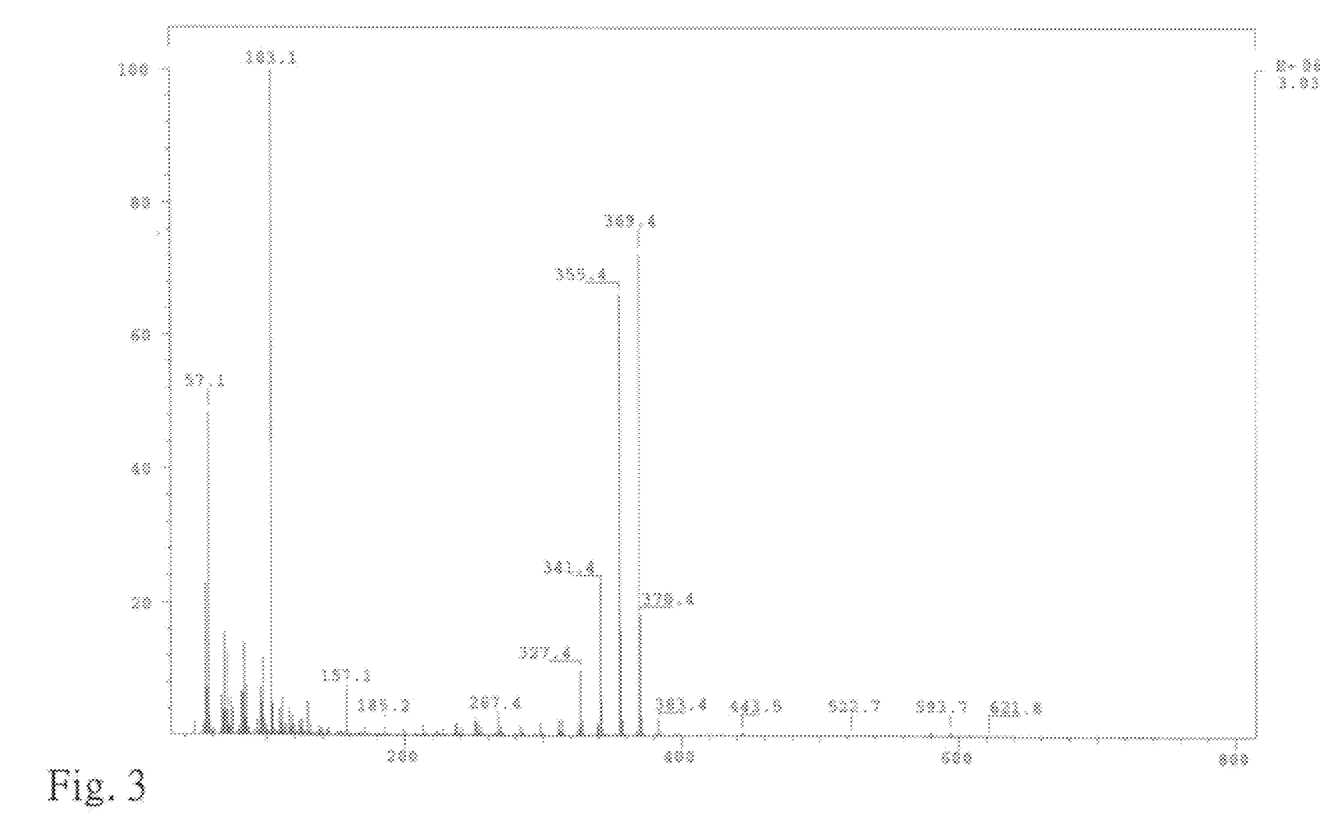
FIG. 3 is the mass spectrogram of the active material from example 2 in this present invention.

Furthermore, the active component was analyzed by electron impact-mass spectrophotometer (EI-MS), and the result is shown as FIG. 3. FIG. 3 disclosed that molecular ion peak [M]+charge-to-mass ratio and relative intensity of the active component, and it shows EI-MS: m/z (%): 370 (20) [M]$^+$, 355(65), 341(22), 327(11), 267(5), 185(3), 157(9), 103 (100), 57 (51).

Example 3: Comparing TNHD of this Present Invention and the Active Component of Example 2

Based on the results of example 1 and 2, it can figure out that structure of compound TNHD of formula (I) from the method of this present invention is the same as the active component produced from example 2 by comparing the compound TNHD from example 1 and the active component from example 2. In other words, compound TNHD from this present invention has function for preventing or treating liver diseases, especially the liver fibrosis related liver diseases. Therefore, effective amount of compound of formula (I) can be taken as a functional material of pharmaceutical composition or daily nutrition supplement.

Furthermore, according to the method revealed in example 2, using 27.7 kg of clam bodies as material only can produce 1 gram of the active component. The productivity of the method in example 2 was merely 0.004%. Comparison of the method in example 2, the method of this present invention only using 2 kg material and it can obtain 260 mg of compound of formula (I). The productivity of the method from this present invention was 13% and it was obviously greater than the conventional method. Accordingly, the method of this present invention can effectively increase productivity of compound of formula (I), at the same time reduce costs of production.

Example 4: Animal Experiment

The 4 weeks-old male C57BL/6 mice were divided into 5 groups and treated with different feeding conditions, wherein the group 1 was the blank control fed with normal diet and water, the group 2 was fed with 45% high-fat diet and water, the group 3 was fed with 45% high-fat diet, water and 10 mg/Kg the compound TNHD, the group 4 was fed with 45% high-fat diet, water and 20 mg/Kg the compound TNHD, and the group 5 was fed with 45% high-fat diet, water and 200 mg/Kg Silymarin. Feeding for 8 weeks, and then all the mice were sacrificed.

According to the standard of dose conversion in Guidance for Industry published FDA (2005), TNHD 10 mg/Kg for mouse is equal to 48.65 mg/day for 60 kg adult, and TNHD 20 mg/Kg for mouse is equal to 97.30 mg/day for 60 kg adult.

Example 5: Weights of the Mice in the Each Group

Figure 4:
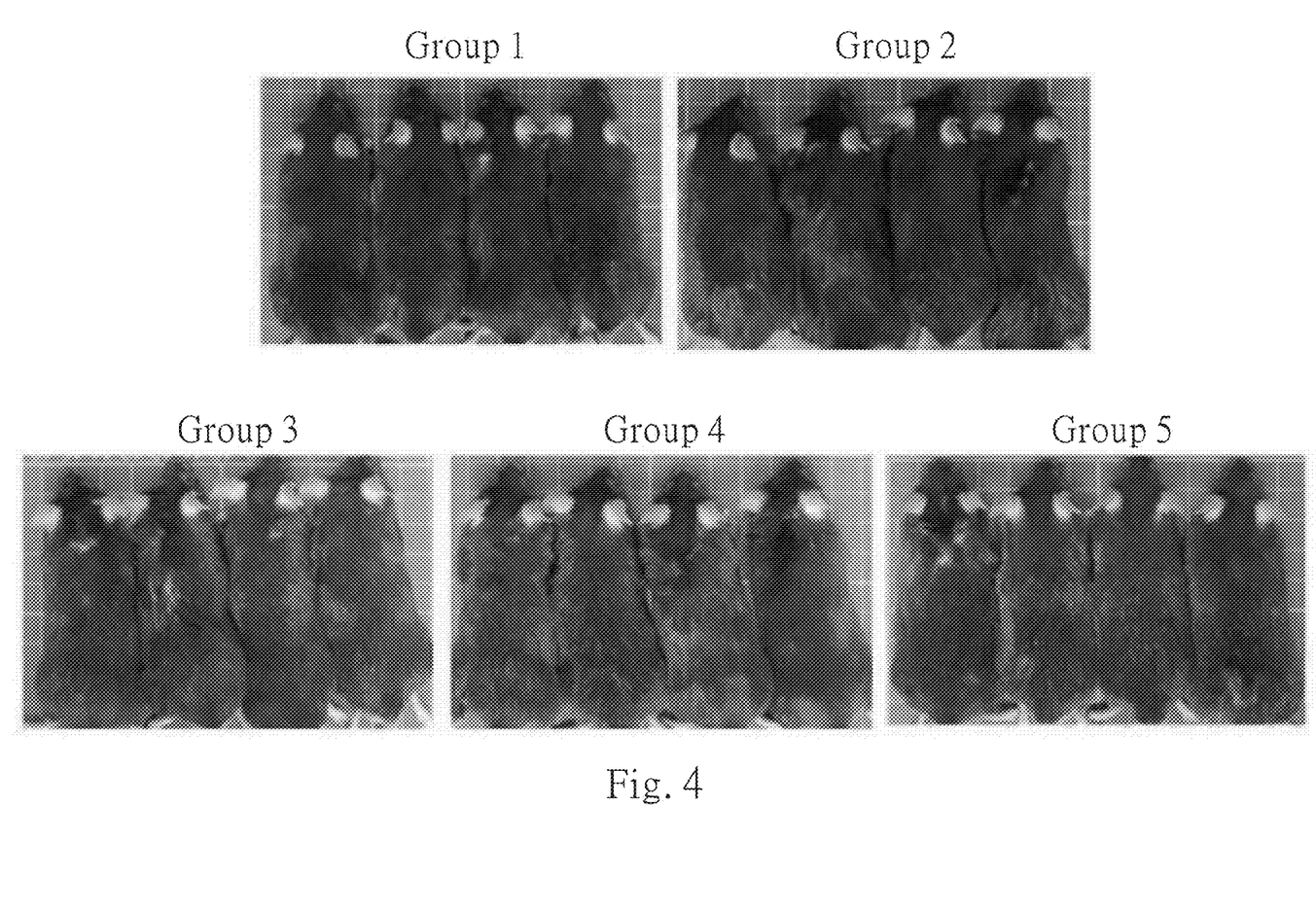
FIG. 4 shows the photographs of the each group at the end of week 8.
Figure 5:
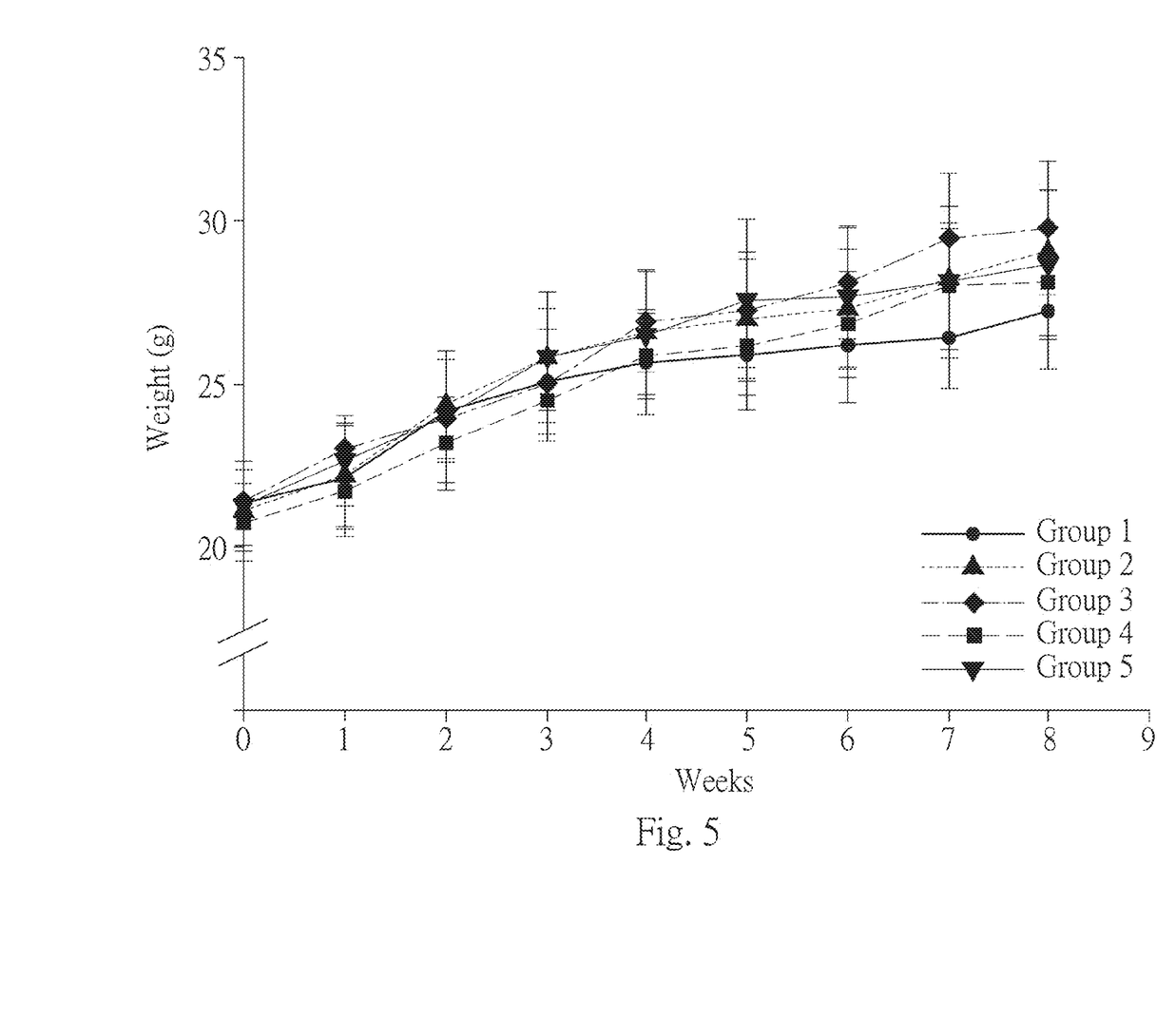
FIG. 5 shows the body weight of the each group weekly.

At the end of the experiment, taking photographs of the each group were shown as FIG. 4. The body weight of the each group was monitored weekly and the average body weight of the each group was shown in FIG. 5.

The body weight and food intake in the each group were recorded in the table 1, wherein the data is expressed as the mean±SE.

TABLE 1

| Body weight and food intake in the each group | | | | | |
|---|---|---|---|---|---|
| | group | | | | |
| | 1 | 2 | 3 | 4 | 5 |
| Initial wight (g) | 21.3 ± 1.3 | 21.1 ± 1.2 | 21.4 ± 1.1 | 20.7 ± 1.1 | 21.3 ± 0.7 |
| Final wight (g) | 26.3 ± 0.9 | 29.6 ± 1.5 | 29.8 ± 2.0 | 28.1 ± 1.6 | 28.7 ± 2.3 |
| Food intake (g/mouse/day) | 5.4 ± 0.1 | 3.7 ± 0.1 | 4.5 ± 0.2 | 3.7 ± 0.2 | 3.5 ± 0.1 |

According to the above results, it shows that feeding with high-fat diet is capable of preparing the mouse model of obesity. By feeding the compound TNHD, it can prevent and inhibit the body weight of obesity mouse to increase, wherein feeding the compound TNHD with high dose is more effective. Furthermore, the compound TNHD is more effective to weight loss than Silymarin.

Therefore, it suggests that the compound TNHD is able to inhibit and prevent the increase of body weight without changing dietary intakes.

Example 6: The Liver of the Each Group

The weights of liver, kidney and spleen of the mice in the each group were measured and recorded in table 2. The macroscopic appearance of the liver from the mice of the each group was shown as FIG. 6. Furthermore, the liver collected from the sacrificed mice in each groups was fixed with formalin. After the fixation, the liver tissue of the each group was paraffin-embedded for histology section and stained by H&E and Surius red for analysis. The results of staining were shown in FIGS. 7 and 8.

TABLE 2

| Organ weights in the each group | | | | | |
|---|---|---|---|---|---|
| | group | | | | |
| | 1 | 2 | 3 | 4 | 5 |
| Liver (g) | 5.43 ± 0.47 | 5.82 ± 0.61 | 5.23 ± 0.84 | 5.63 ± 0.61 | 4.96 ± 0.66 |
| Kidney (g) | 1.52 ± 0.11 | 1.58 ± 0.17 | 1.51 ± 0.25 | 1.63 ± 0.24 | 1.61 ± 0.14 |
| Spleen (g) | 0.44 ± 0.23 | 0.34 ± 0.05 | 0.30 ± 0.04 | 0.53 ± 0.36 | 0.43 ± 0.13 |

Figure 6:
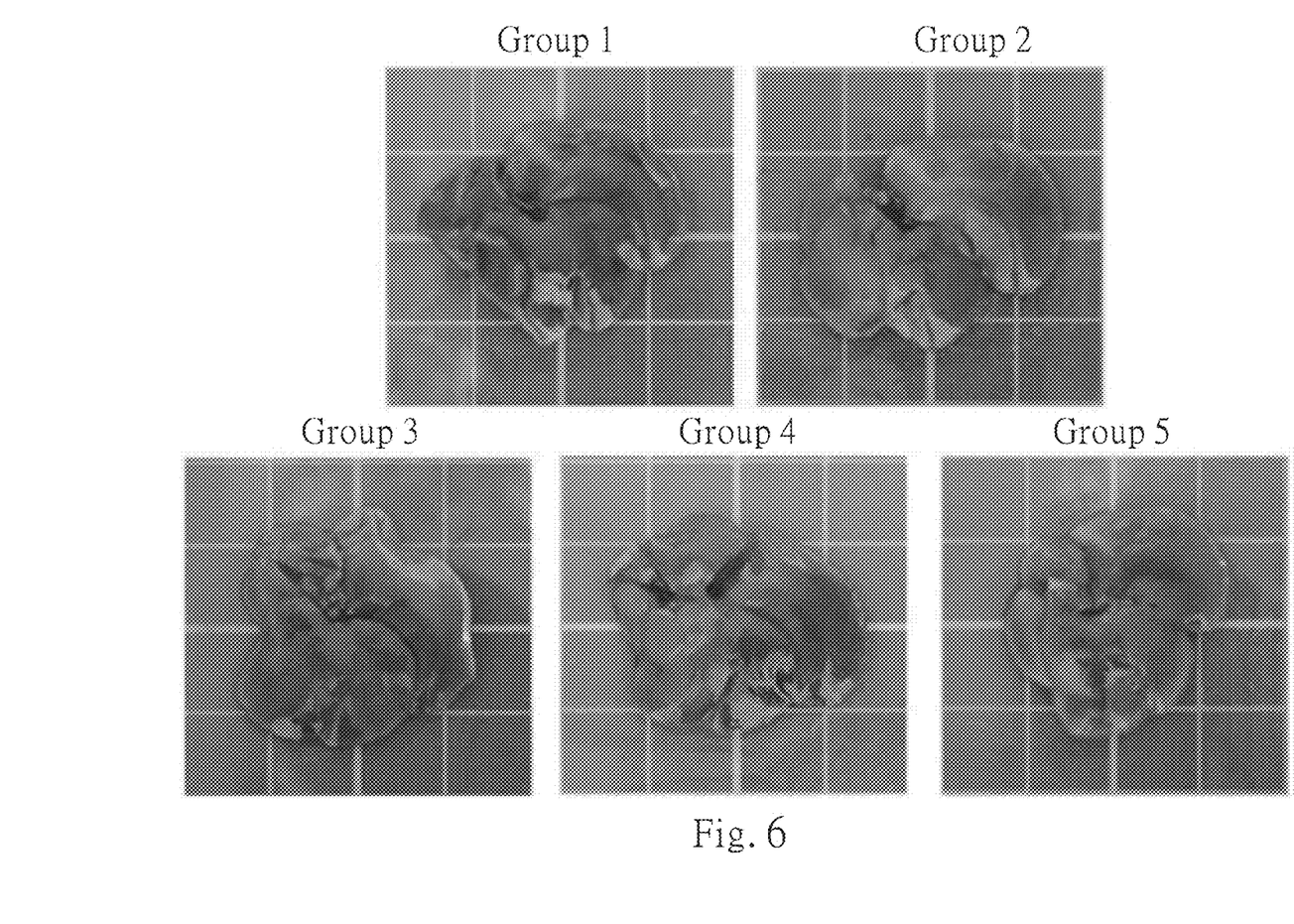
FIG. 6 shows the appearance of the liver from the each group.

Please see table 2 and FIG. 6. Comparing to the group 1, the color of liver from the group 2 is with yellow and the weight was increased. In the group 3 or group 4, the liver shows the red color and has smooth surface.

Figure 7:
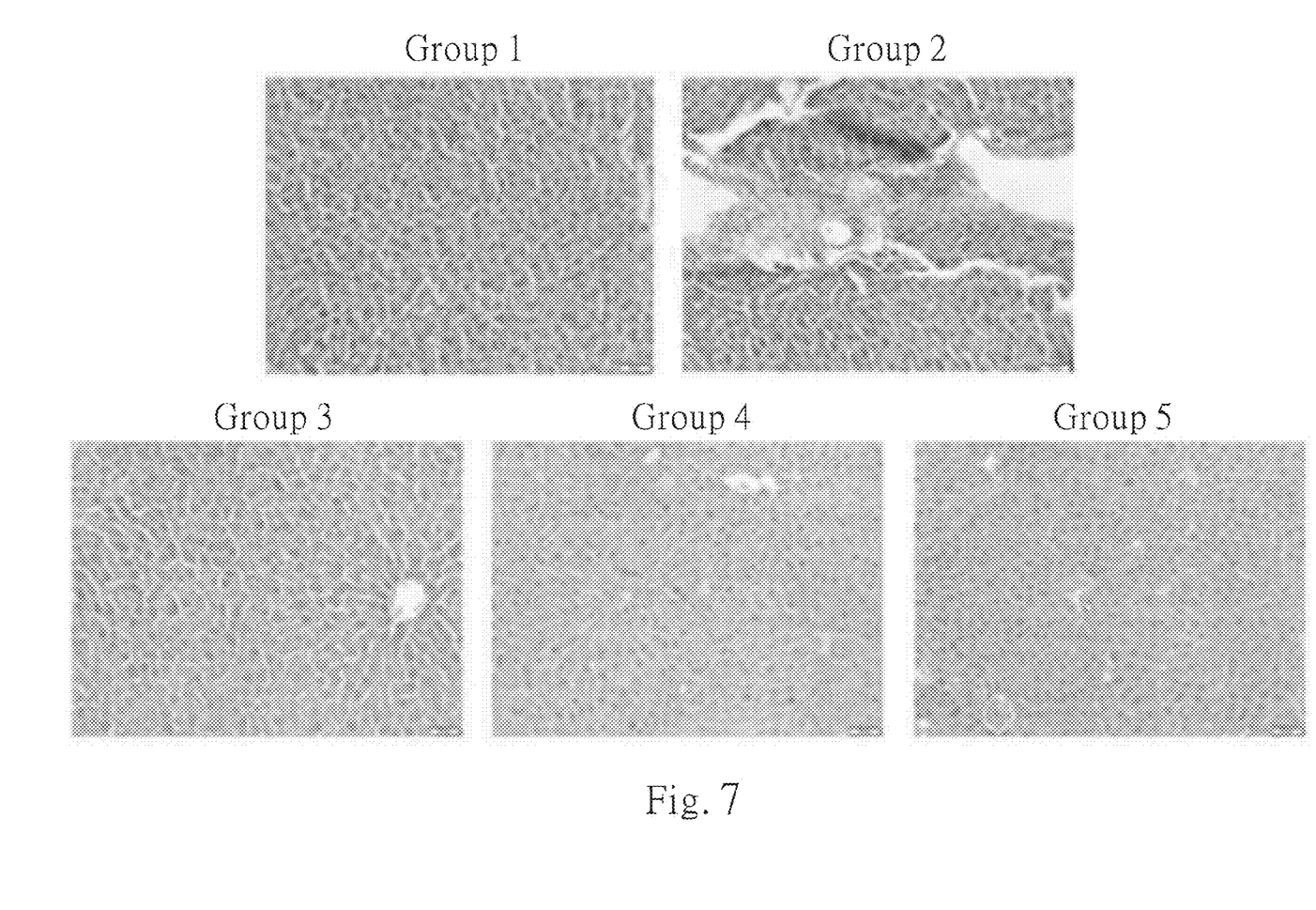
FIG. 7 shows the result of H&E staining in liver from the each group.
Figure 8:
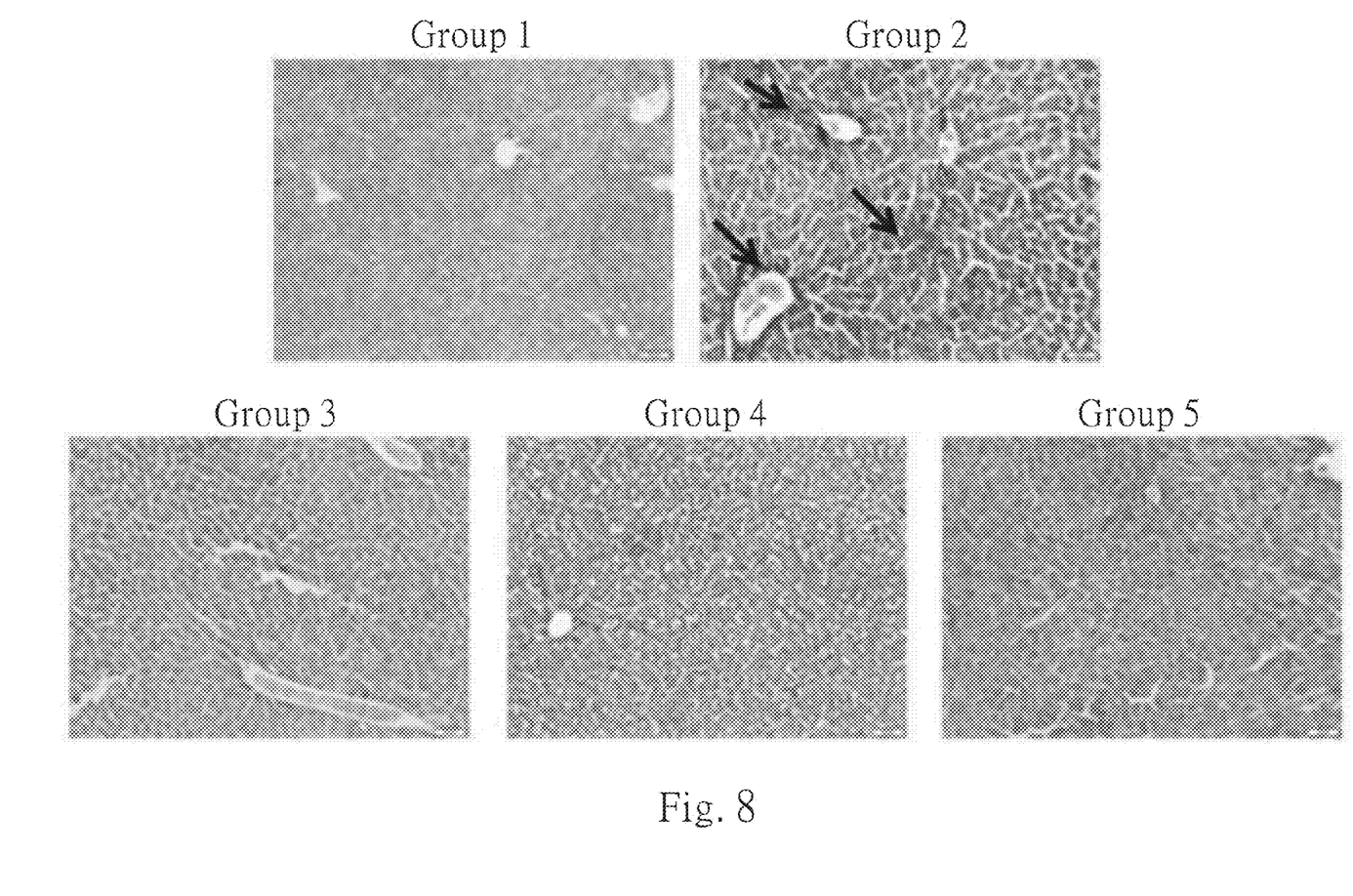
FIG. 8 shows the result of Surius red staining in liver from the each group.
Figure 9:
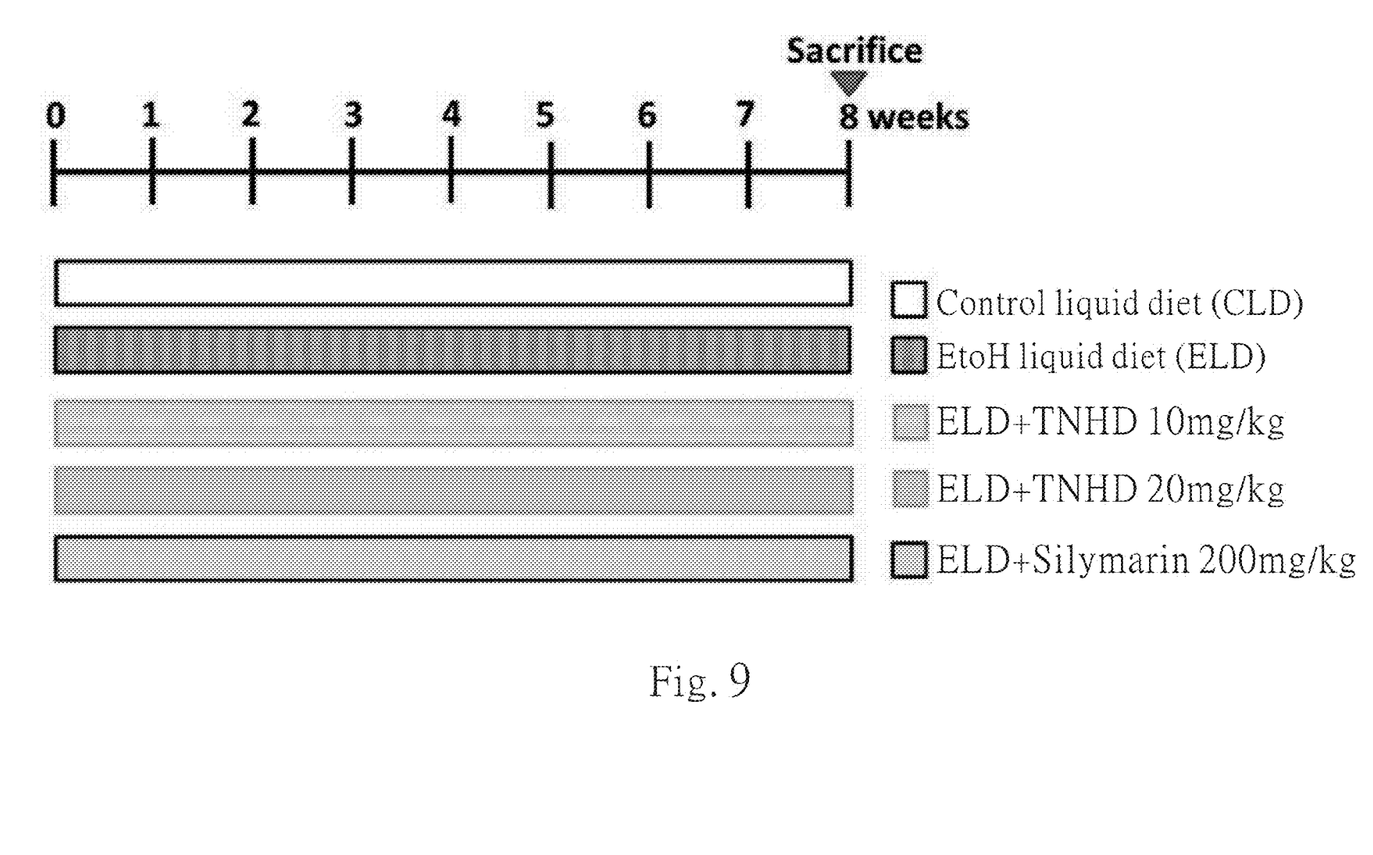
FIG. 9 shows the flow chart for the other animal experiment.
Figure 10:
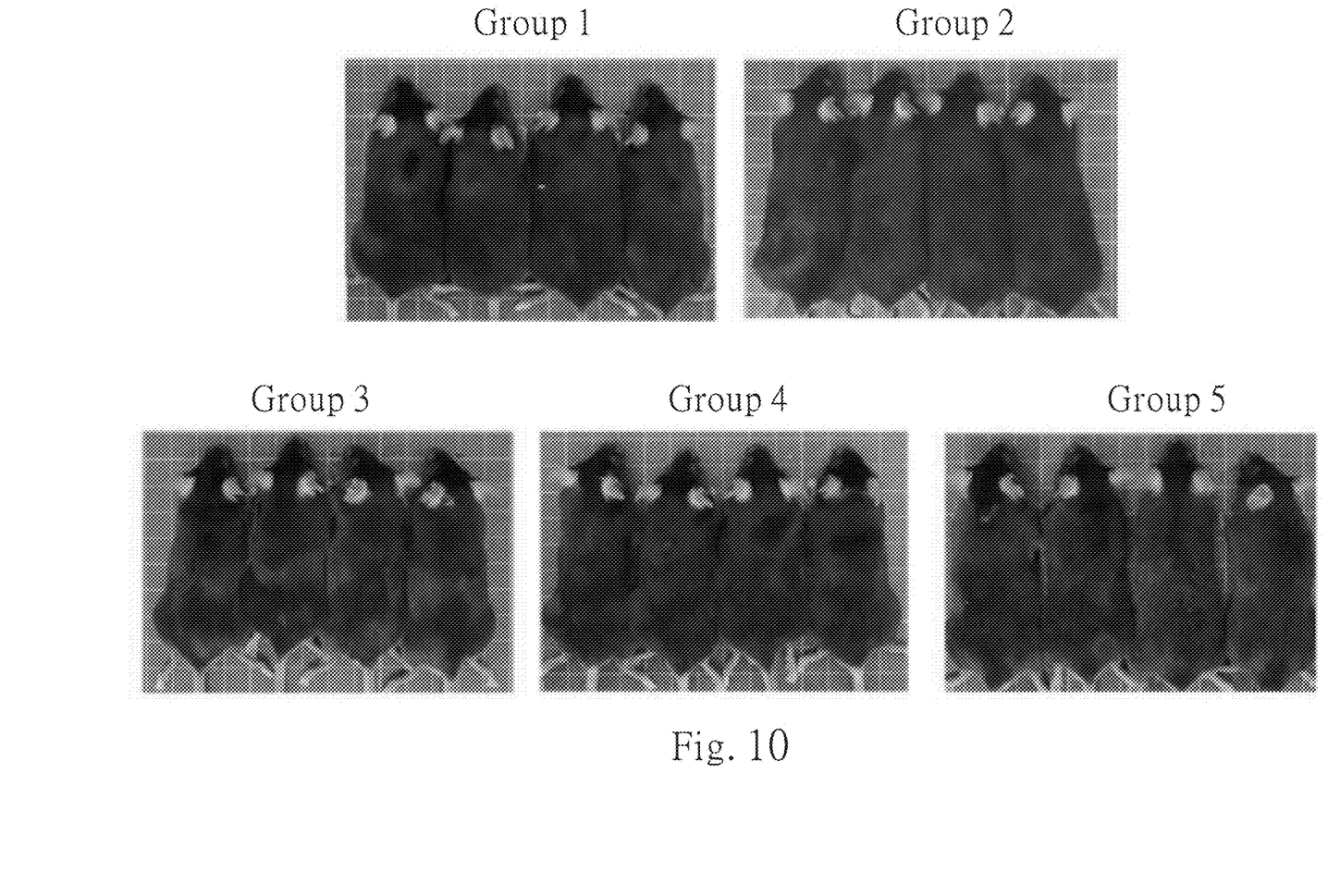
FIG. 10 shows the photographs of the each group in the other animal experiment at the end of week 8.
Figure 11:
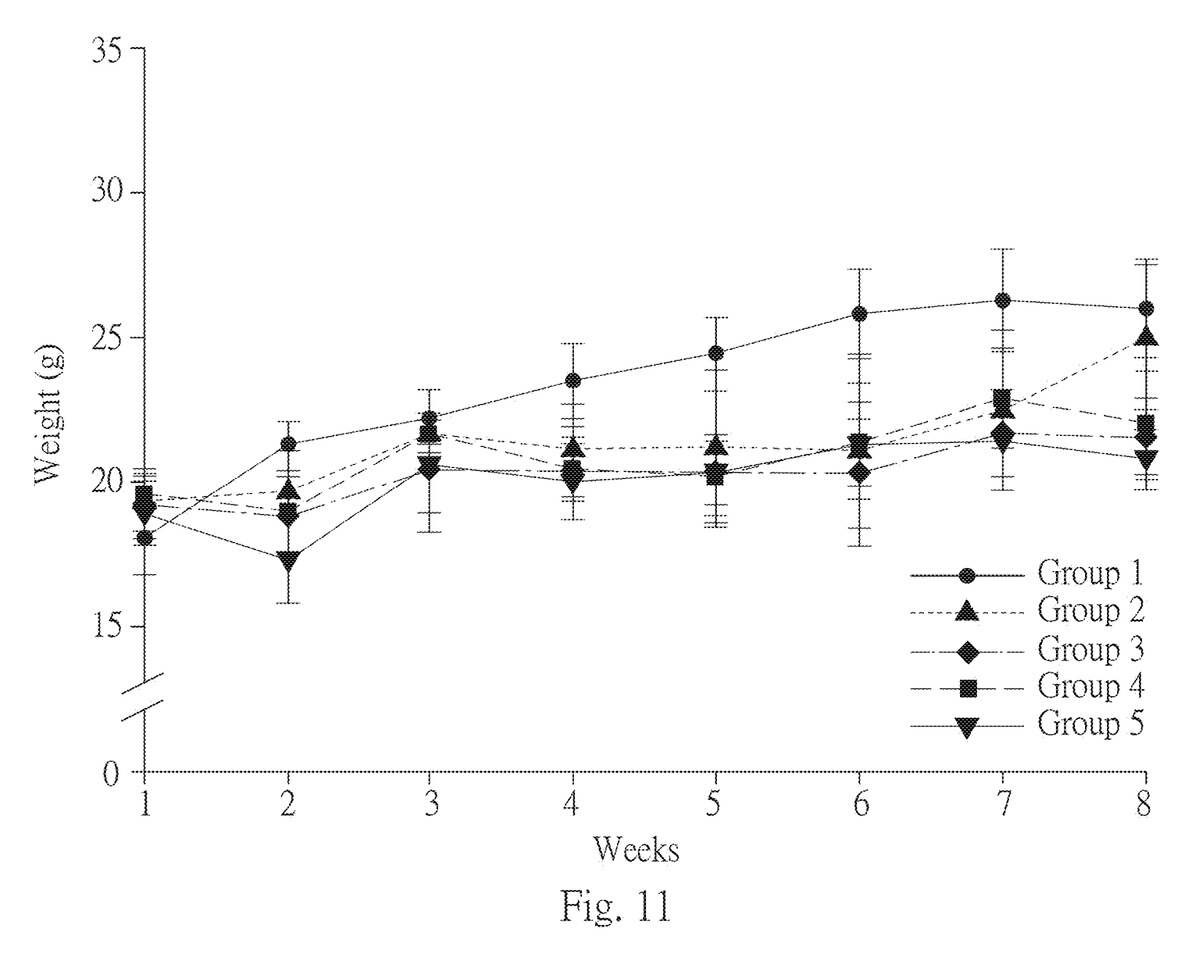
FIG. 11 shows the body weight of the each group in the other animal experiment.
Figure 12:
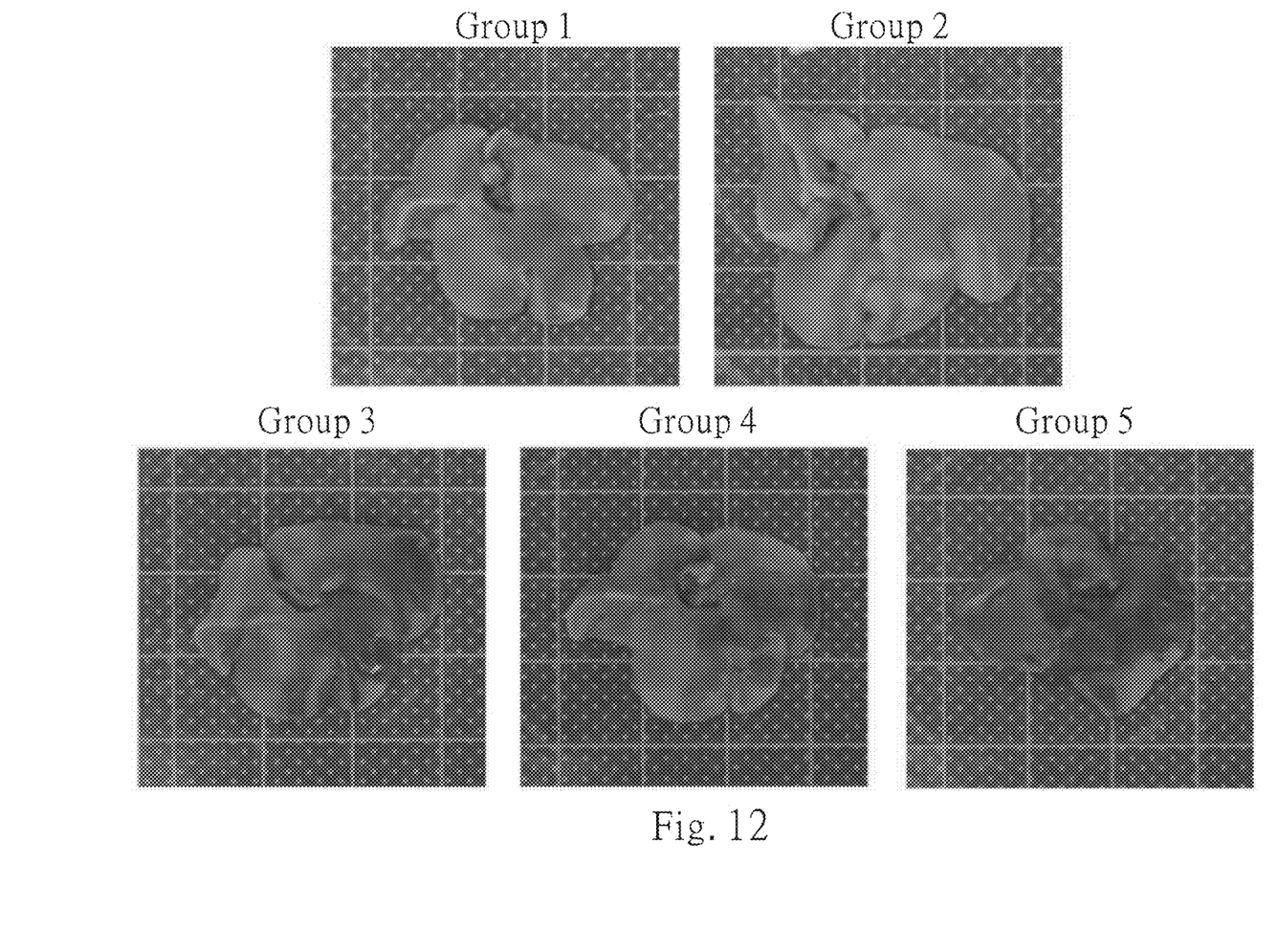
FIG. 12 shows the appearance of the liver from the each group in the other animal experiment.
Figure 13:
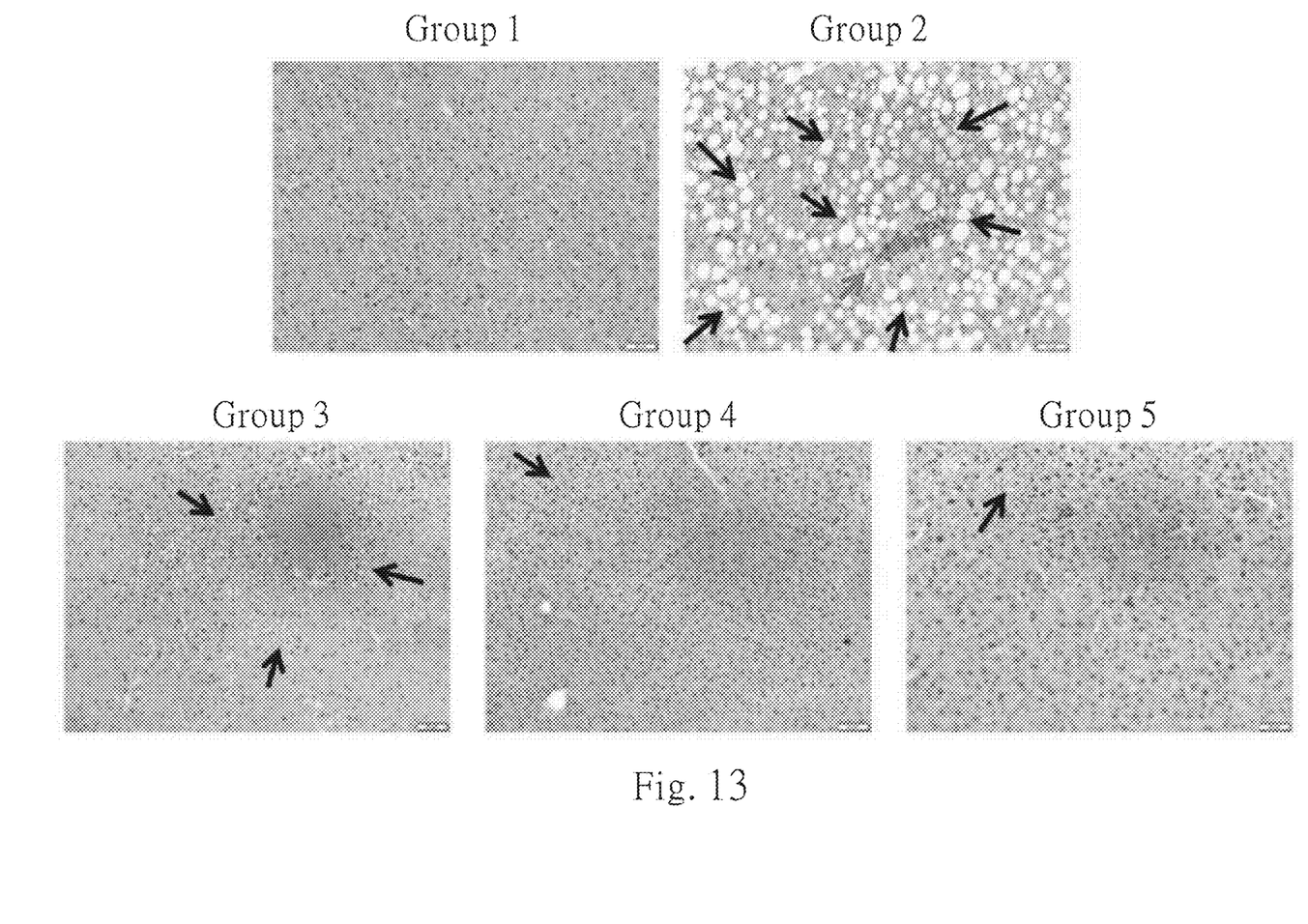
FIG. 13 shows the result of H&E staining in liver from the each group in the other animal experiment.
Figure 14:
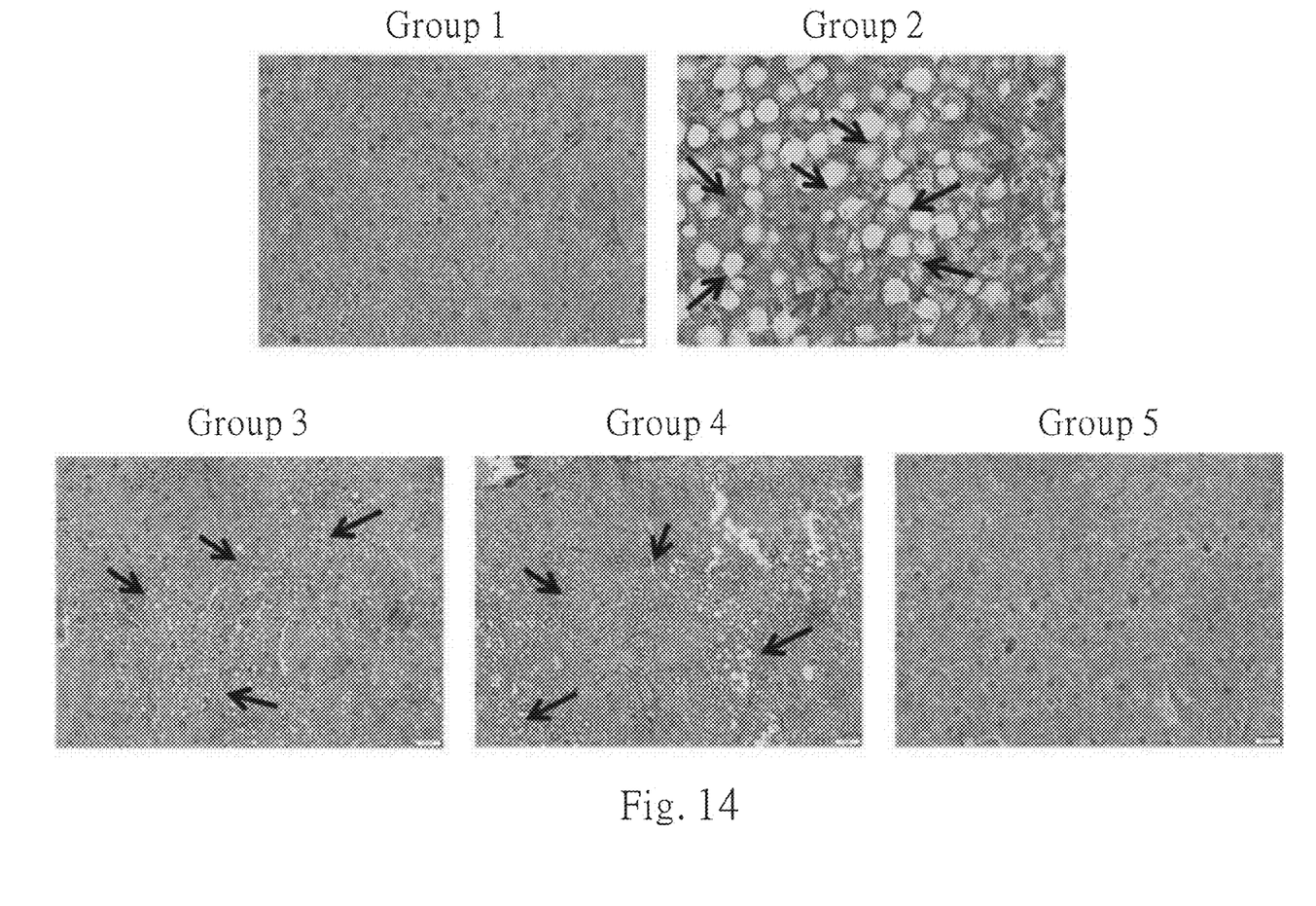
FIG. 14 shows the result of Surius red staining in liver from the each group in the other animal experiment.

Please further see the FIGS. 7 and 8. Comparing the group 1 and group 2, it shows that the hepatocytes arrange loosely and the fat accumulates in the liver from the group 2. Moreover, the nodules were formed in the liver of the group 2. Feeding high fat diet let excess fat accumulate in liver to cause liver damage such as inflammation, fatty liver and liver fibrosis.

By administering the compound TNHD to the subject with high fat diet, it can inhibit the lipid accumulation in the liver effectively. In other words, the compound TNHD of the present invention is able to treating or/and preventing the fatty liver, liver fibrosis and liver fibrosis, and the effect will be better with administering the compound TNHD in high dose.

In the other animal experiment using the fatty liver and obesity animal model prepared by ethanol-containing diet (Lieber-DeCarli), it shows the same results as above. The experimental design and results were shown in FIGS. 9 to 14. According to the results of FIGS. 9 to 14, it indicates the compound TNHD is effective to treat or/and prevent obesity, fatty liver or liver damage caused by alcohol.

According to the above example, it can prove the compound TNHD of the present invention can be effective to treat and/or prevent the obesity and fatty liver. And the method of producing TNHD disclosed by the present invention can effectively increase productivity and lower the costs. Furthermore, the effective dose of TNHD to an adult is 40 mg/day to 100 mg/day, wherein the better dose is about 90~100 mg/day. It should be understood that the above-mentioned detailed description and specific examples, while indicating preferred embodiments of the invention, are given by way of illustration only. Various changes and modifications within the spirit and scope of the invention will become apparent to those skilled in the art from this detailed description. All such modifications as would be obvious to one skilled in the art are intended to be included within the scope of the following claims.

What is claimed is:

1. A method for treating obesity, comprising administering an adult human in need of such treatment an amount of 97.30 mg/day of a compound of formula (I):

effective to inhibit the increase of body weight of the adult human.

2. The method according to claim 1, wherein the amount of the compound of formula (I) is 97.30 mg/day.

3. The method according to claim 1, wherein the compound of formula (I) is produced by acetalization reaction of the compounds of formula (II):

and formula (I11):

4. The method according to claim 3, wherein an acidic catalyst is used during the acetalization reaction.

5. The method according to claim 3, wherein the mixture containing the compound of formula (I) can be purified by separation process.